United States Patent
Ferrigolo et al.

(10) Patent No.: US 8,764,692 B2
(45) Date of Patent: Jul. 1, 2014

(54) KNEE BRACE WITH LIGHTWEIGHT STRUCTURE

(75) Inventors: Moreno Ferrigolo, Dossobuono (IT); Alberto Turrini, Castel D'Azzano (IT); Edward G. Wilbourne, Summerfield, NC (US)

(73) Assignee: F.G.P. SRL, Dossobuono (IT)

( * ) Notice: Subject to any disclaimer, the term of this patent is extended or adjusted under 35 U.S.C. 154(b) by 377 days.

(21) Appl. No.: 11/616,238

(22) Filed: Dec. 26, 2006

(65) Prior Publication Data
US 2007/0213648 A1    Sep. 13, 2007

(30) Foreign Application Priority Data

Mar. 9, 2006  (EP) ..................... 06425159

(51) Int. Cl.
*A61F 5/00* (2006.01)
*A61F 5/37* (2006.01)
*A61F 5/01* (2006.01)

(52) U.S. Cl.
CPC ....... *A61F 5/0123* (2013.01); *A61F 2005/0134* (2013.01)
USPC .................. 602/26; 602/16; 602/23; 128/882

(58) Field of Classification Search
USPC ......... 602/26, 16, 23, 20; 128/882, 878; 2/22; 16/901, 18 R, 24, 28, 26, 43, 224
See application file for complete search history.

(56) References Cited

U.S. PATENT DOCUMENTS

| | | | | |
|---|---|---|---|---|
| 2,753,586 A * | 7/1956 | Metz | ............................. | 16/18 R |
| 3,297,028 A * | 1/1967 | Murray | ........................... | 602/61 |
| 3,669,105 A * | 6/1972 | Castiglia | ......................... | 602/16 |
| 4,428,369 A * | 1/1984 | Peckham et al. | ................ | 602/16 |
| 4,487,200 A | 12/1984 | Feanny et al. | | |
| 5,316,547 A * | 5/1994 | Gildersleeve | ................... | 602/26 |
| 5,399,154 A * | 3/1995 | Kipnis et al. | .................... | 602/26 |
| 5,458,565 A | 10/1995 | Tillinghast et al. | | |
| 5,527,268 A * | 6/1996 | Gildersleeve et al. | .......... | 602/26 |
| 5,554,104 A * | 9/1996 | Grim | ................................. | 602/8 |
| 5,599,286 A * | 2/1997 | Labelle et al. | .................. | 602/19 |
| 5,679,052 A * | 10/1997 | Rucki | .............................. | 450/57 |
| 6,328,707 B1 * | 12/2001 | Lampkins | ....................... | 602/23 |
| 6,752,775 B2 * | 6/2004 | Seligman et al. | ............... | 602/16 |
| 7,011,640 B2 * | 3/2006 | Patterson et al. | ............... | 602/13 |
| 2004/0068215 A1 | 4/2004 | Adelson et al. | | |
| 2005/0234379 A1 * | 10/2005 | Patterson et al. | ............... | 602/26 |

* cited by examiner

*Primary Examiner* — Victoria J Hicks
(74) *Attorney, Agent, or Firm* — Greenberg Traurig, LLP

(57) ABSTRACT

A knee brace for the correction of abnormalities of the knee such as varus or valgus knee, or for the various forms of osteoarthritis, consisting of a support structure with a sole direction of development, that is to say it comprises a single upright (11) for the femoral area and a single upright (12) for the tibial area, these uprights (11, 12) being connected and hinged to a single articulated joint (13), which can be positioned close to one side of the knee, generally the outer side in the case of varus knee or the inner side in the case of valgus knee.

2 Claims, 3 Drawing Sheets

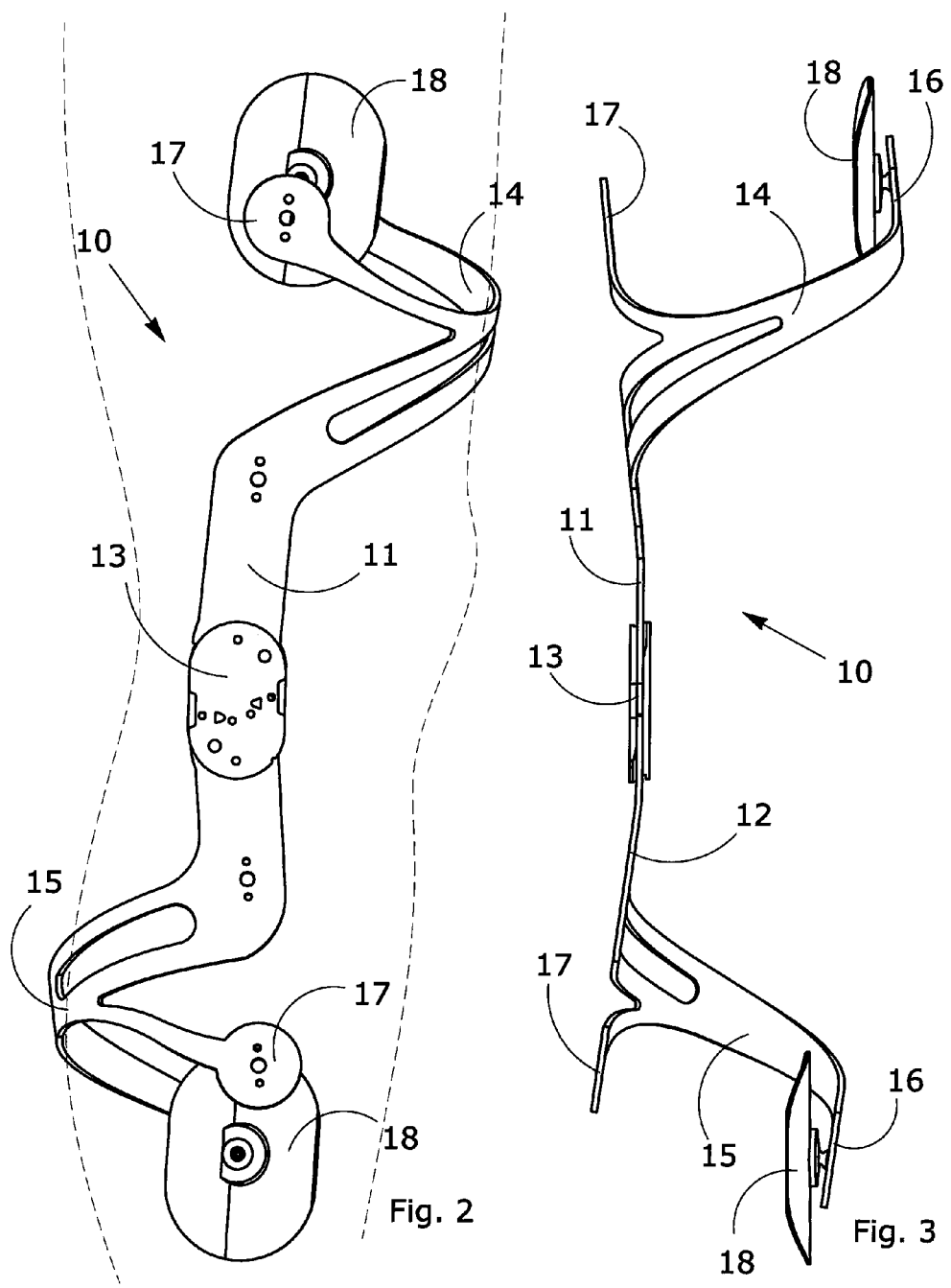

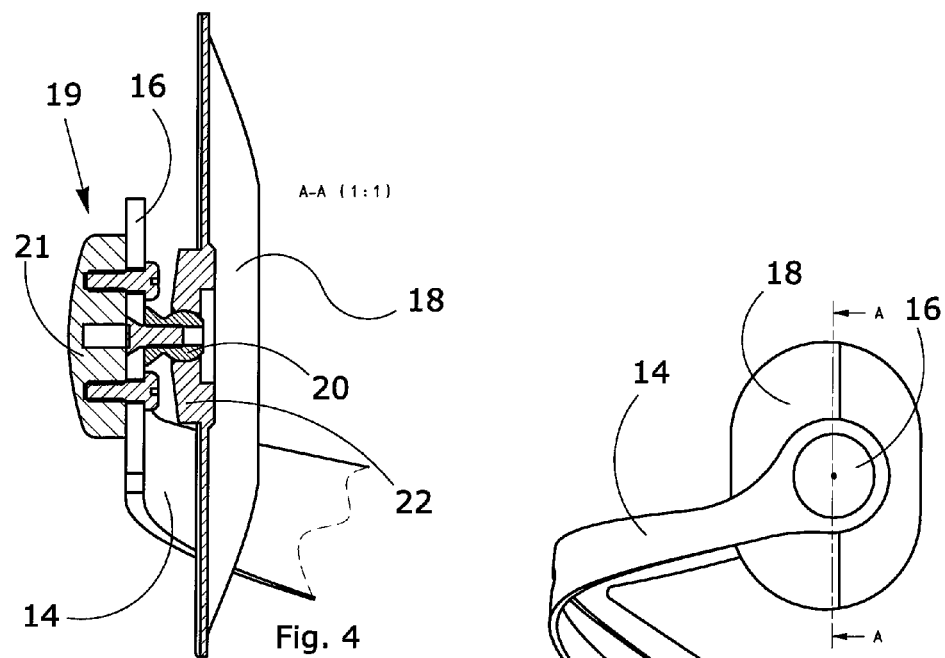
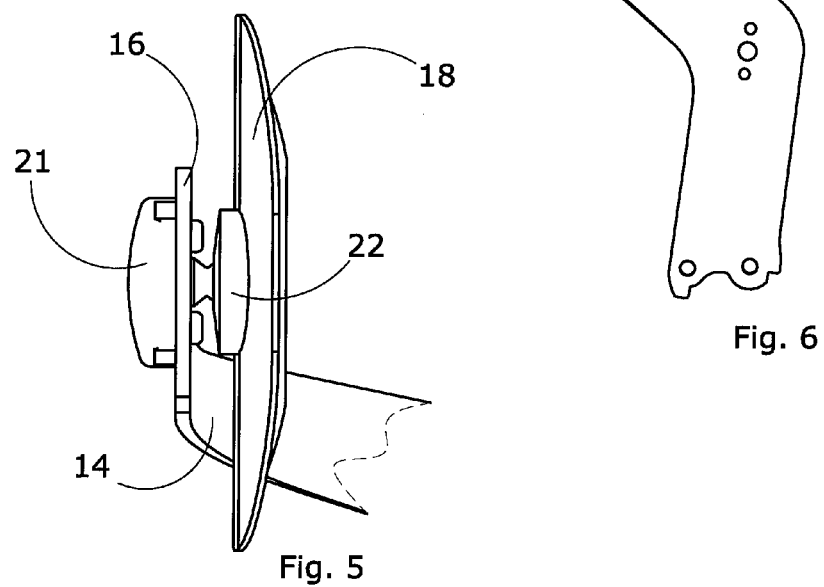

KNEE BRACE WITH LIGHTWEIGHT STRUCTURE

RELATED APPLICATION DATA

This application claims the benefit of priority to European Application Number EP06425159, filed on Mar. 7, 2006 and entitled "Knee Brace With Lightweight Structure", which is incorporated by reference in the present application in its entirety.

TECHNICAL FIELD

This invention concerns a knee brace with a lightweight structure.

More specifically, this invention refers to a knee brace with a very simple and basic structure, although it includes all the components for fixing it to the leg and to control the angular excursion of the knee joint both when the leg is extended and when it is flexed.

The solution according to this invention is particularly useful since it is made using a small number of essential components which on one hand make it possible to limit production costs and on the other to improve the wearing conditions, since the very lightweight structure means that the user will find it extremely practical and easy to wear, precisely because it is such a basic device.

Thanks to its structure, the knee brace in question also allows it to be used to correct certain knee abnormalities, such as varus or valgus knee, or for forms of osteoarthritis.

This knee brace can be used to correct or support knee abnormalities, such as valgus or varus knee, but also in post-traumatic treatment and in pre and postoperative conditions.

This invention can be applied in the medical industry with particular reference to the orthopedic sector and to manufacturers of prostheses and walkers.

BACKGROUND ART

The use is known of orthopedic type knee braces, consisting of structures which enclose the femoral and tibial areas of the leg, equipped with a coupling device normally designed to allow adjustment of the angular excursion in order to ensure a correct end-of-stroke both when the tibia is extended and when it is flexed with respect to the femur.

According to background art, knee braces generally consist of femoral and tibial uprights joined together by a pair of hinged discs, each integral with a respective upright which is in turn fixed to the leg of the user.

Precisely because of the way in which they are made, the structure of known knee braces is notoriously impractical to wear and, above all, due to a plurality of femoral and tibial uprights, is particularly heavy, even if structural components made from lightweight aluminium alloys or other lightweight metal alloys are used.

Traditional knee braces are therefore poorly tolerated because of their heaviness and their cumbersome dimensions, compromising the comfort of the wearers and causing them pointless inconvenience, especially when suffering from disorders, as for example in the case of valgus or varus knee, which only require lateral and internal and/or external pressure.

In addition, known knee braces, like those currently designed, are manufactured with a considerable outlay on materials and labour since they consist of structures and frames which are often very complex and cumbersome even if they do ensure a grip on the leg. This is to the detriment of the purchase price, which is often excessive for the user who is, therefore, unmotivated to make the purchase.

Another drawback concerns the fact that for some disorders or for certain corrective measures, such as for example in the case of varus or valgus knee or in forms of osteoarthritis, and above all for less serious and problematic disorders, it would be more appropriate to have a lightweight and non-cumbersome structure. This is almost impossible with the current type of knee braces, all completely enclosing the leg and equipped with uprights on both sides.

DESCRIPTION OF THE INVENTION

This invention proposes to provide a knee brace with a lightweight structure that can eliminate or significantly reduce the problems described above.

This invention also proposes to provide a safe and reliable knee brace for the treatment of patients afflicted by varus or valgus knee, or by various forms of osteoarthritis.

This is achieved by means of a knee brace with a lightweight structure with the features described in the main claim.

The dependent claims describe advantageous embodiments of the invention.

The knee brace according to the invention substantially comprises a support structure with a sole direction of development, that is to say it comprises a single upright for the femoral area and a single upright for the tibial area. These uprights are connected and hinged to a single articulated joint, which can be positioned close to one side of the knee, generally the outer side for a varus knee or the inner side for a valgus knee.

The ends of the two uprights that make up the knee brace according to the invention are shaped to form a structure that wraps around the front half of the femoral area and the rear half of the tibial area. They also comprise appendages which can be fitted with thrust and elastic compression adjustable elements.

According to the invention, the knee brace is covered with finishing material and fastenings, such as soft cloth, to which straps are applied that can be blocked with buckle type or Velcro systems.

The articulated joint that holds the two uprights together is equipped with 2 pivots designed to ensure appropriate mobility achieved by the presence of multiple rotation centres.

To ensure appropriate freedom of movement of the limb, the structure develops on one side only of the knee, in order to allow correct mutual oscillation between the tibia and the femur when the leg is extended and when it is flexed.

The structure of the orthopedic brace according to the invention can be made from lightweight metal alloy or high resistance composite plastic.

DESCRIPTION OF THE DRAWINGS

Other features and advantages of the invention will become evident on reading the description given below of one embodiment of the invention, given as a non-binding example, together with the help of the accompanying drawings in which:

FIG. 2 shows a prospective side view of the knee brace in FIG. 1 according to the invention;

FIG. 3 shows the same knee brace shown from the front;

FIGS. 4 to 6 are schematic views showing the configuration of the thrust pads covered in soft cloth, attached to the ball joint.

DESCRIPTION OF ONE EMBODIMENT

Figure 1:
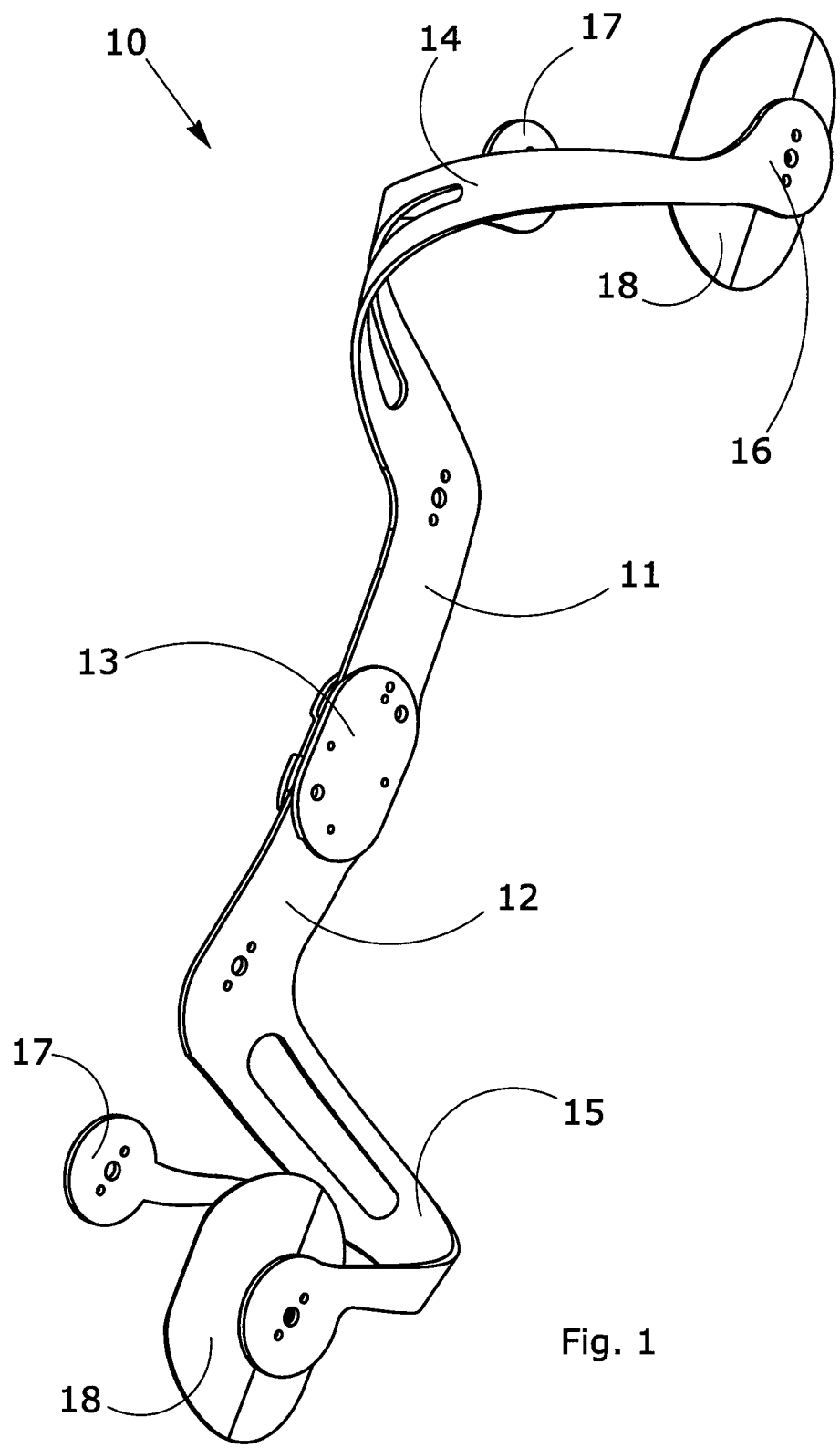
FIG. 1 represents a prospective front view of the overall frame of a knee brace according to the invention in a slightly inclined position.

With reference first of all to FIG. 1, the reference number 10 indicates a knee brace in general, in the case in question a knee brace with a lightweight structure to be used in particular in cases of varus or valgus knee, or in the various forms of osteoarthritis or in other cases in which a not excessively constrictive restraint of the knee joint is required, with lateral thrust.

The knee brace 10 thus substantially comprises a pair of single uprights, that is to say a femoral upright 11 and a tibial upright 12.

The femoral upright 11 and the tibial upright 12, which are positioned along the leg on one side of the knee joint are attached together by an articulated joint 13 which holds the uprights in position and is equipped with 2 pivots designed to ensure appropriate mobility by the presence of multiple centres of rotation.

To ensure appropriate freedom of movement of the limb, the structure develops on one side only of the knee, in order to allow correct mutual oscillation between the tibia and the femur when the leg is extended and when it is flexed.

As can be seen in FIG. 1, the knee brace according to the invention substantially consists of a support structure with a sole direction of development, that is to say it comprises a single upright for the femoral area 11 and a single upright for the tibial area 12.

The uprights 11 and 12 are connected and hinged to a single articulated joint 13, which can be positioned close to one of the sides of the knee, generally the outer side for a varus knee or the inner side for a valgus knee.

The ends of the two uprights that make up the knee brace according to the invention are shaped to form a semicircular structure 14 that wraps around the front half of the femoral area and another semicircular structure 15 that wraps around the rear half of the tibial area.

The semicircular structures 14 and 15 also comprise substantially semicircular appendages or pads 16 and 17 which can be fitted with thrust and elastic compression adjustable elements 18.

According to the invention, the knee brace is covered with finishing material and fastenings not shown as they are already known, for example in soft cloth, to which straps are applied that can be blocked with buckle type or Velcro systems.

As can be seen in FIGS. 4 to 6, the thrust and elastic compression adjustable elements 18, fitted on the substantially semicircular appendages or pads 16 of the two semicircular structures 14 and 15, are mounted on a hinged structure indicated overall with 19.

As can be seen in the cross-section in FIG. 4, the jointed structure 19 substantially consists of a spherical head 20, positioned on a base 21 integral with the end 16 of the knee brace.

The spherical head 20 is compressed inside a housing in the support 22 which holds the thrust and elastic compression adjustable elements 18.

This assembly system of the soft thrust pad 18 allows it to rest against the leg while perfectly following its inclination.

As can be noted in the figures and from the description, the structure according to the invention allows it to be worn in comfort while exerting lateral pressure on the knee joint.

Being designed to correct abnormalities such as varus or valgus knee, the described structure can naturally be fitted with the articulated joint and the uprights positioned on the inside or the outside of the knee joint, that is to say in two separate versions that can be used in the two different abnormalities.

The frame of the knee brace can be made from lightweight metal alloy or high resistance composite plastic.

The invention is described above with reference to a preferred embodiment. It is nevertheless clear that the invention is susceptible to numerous variations that lie within the framework of technical equivalents.

The invention claimed is:

1. A knee brace for correction of abnormalities of a knee that is a varus or a valgus knee, or for correction of various forms of osteoarthritis, wherein said knee has a femoral area and a tibial area, and an outer side and an inner side of the varus knee or the valgus knee, comprising:

a single upright for the femoral area of the knee wherein said femoral area has a front half and a rear half and a single upright for the tibial area of the knee wherein said tibial area has a front half and a rear half, the single uprights being connected and hinged to a single articulated joint which can be positioned close to one side of the knee, generally the outer side of the varus knee or the inner side of the valgus knee, each of said single uprights having two free ends remote from said single articulated joint at opposite directions from each other, wherein the two free ends of each of the single uprights which are positioned in opposite directions with respect to said single articulated joint are each shaped and fitted with a substantially semicircular structure, one of which is configured to wrap around the front half of the femoral area of the knee and another that is configured to wrap around the rear half of the tibial area of the knee, each of the substantially semicircular structures including a substantially semicircular appendage or pad to be positioned on a corresponding opposite side of a leg, the substantially semicircular appendage or pad of each substantially semicircular structure comprising said substantially semicircular appendage or pad being covered in soft cloth and mounted on a jointed hinged structure thereby providing a thrust and elastic compression adjustable element.

2. The knee brace of claim 1 wherein said jointed hinged structure of said thrust and elastic compression adjustable element has a spherical ball, positioned on a base integral with the substantially semicircular appendage or pad of the knee brace and extending from said base toward a housing in a support which holds said thrust and elastic compression adjustable element, whereby said spherical ball is compressed within a ball shaped socket thereby providing a ball joint inside said housing in said support which holds said thrust and elastic compression adjustable element, said spherical ball being confined in said ball shaped socket within said housing, said thrust and elastic compression adjustable element being pivotable about said ball joint in an arcuate direction thereby providing a thrust and elastic compression adjustable element.

* * * * *